US009687527B2

(12) United States Patent
Prestrelski et al.

(10) Patent No.: US 9,687,527 B2
(45) Date of Patent: Jun. 27, 2017

(54) STABLE GLUCAGON FORMULATIONS FOR THE TREATMENT OF HYPOGLYCEMIA

(71) Applicants: Steven Prestrelski, San Diego, CA (US); Wei-Jie Fang, Aurora, CO (US); John F. Carpenter, Littleton, CO (US); John Kinzell, San Rafael, CA (US)

(72) Inventors: Steven Prestrelski, San Diego, CA (US); Wei-Jie Fang, Aurora, CO (US); John F. Carpenter, Littleton, CO (US); John Kinzell, San Rafael, CA (US)

(73) Assignees: THE REGENTS OF THE UNIVERSITY OF COLORADO, A BODY CORPORATE, Denver, CO (US); XERIS PHARMACEUTICALS, INC., Austin, TX (US)

( * ) Notice: Subject to any disclaimer, the term of this patent is extended or adjusted under 35 U.S.C. 154(b) by 0 days.

(21) Appl. No.: 14/186,367

(22) Filed: Feb. 21, 2014

(65) Prior Publication Data
US 2014/0171364 A1   Jun. 19, 2014

Related U.S. Application Data

(63) Continuation of application No. 13/186,275, filed on Jul. 19, 2011, now abandoned.

(60) Provisional application No. 61/365,637, filed on Jul. 19, 2010.

(51) Int. Cl.
A61K 38/26 (2006.01)
A61K 47/36 (2006.01)
A61K 9/00 (2006.01)
A61K 47/26 (2006.01)
A61K 9/19 (2006.01)
A61K 47/02 (2006.01)
A61K 47/12 (2006.01)
A61K 47/18 (2017.01)
A61K 47/40 (2006.01)

(52) U.S. Cl.
CPC ............ A61K 38/26 (2013.01); A61K 9/0019 (2013.01); A61K 9/19 (2013.01); A61K 47/02 (2013.01); A61K 47/12 (2013.01); A61K 47/183 (2013.01); A61K 47/26 (2013.01); A61K 47/36 (2013.01); A61K 47/40 (2013.01)

(58) Field of Classification Search
CPC ........ A61K 9/0019; A61K 9/19; A61K 38/26; A61K 47/02; A61K 47/40; A61K 47/183; A61K 47/26; A61K 47/36; A61K 47/12
See application file for complete search history.

(56) References Cited

U.S. PATENT DOCUMENTS

| | | |
|---|---|---|
| 3,016,895 A | 1/1962 | Sein |
| 4,608,764 A | 9/1986 | Leuenberger |
| 4,848,094 A | 7/1989 | Davis et al. |
| 4,927,571 A | 5/1990 | Huang et al. |
| 5,031,336 A | 7/1991 | Diesner et al. |
| 5,092,843 A | 3/1992 | Monroe et al. |
| 5,208,998 A | 5/1993 | Oyler, Jr. |
| 5,260,306 A | 11/1993 | Boardman et al. |
| 5,716,640 A | 2/1998 | Kamei et al. |
| 5,932,547 A | 8/1999 | Stevenson et al. |
| 5,977,082 A | 11/1999 | Gatti et al. |
| 6,001,336 A | 12/1999 | Gordon |
| 6,051,256 A | 4/2000 | Platz et al. |
| 6,199,297 B1 | 3/2001 | Wisniewski |
| 6,253,463 B1 | 7/2001 | Hansen |
| 6,264,990 B1 | 7/2001 | Knepp et al. |
| 6,290,991 B1 | 9/2001 | Roser et al. |
| 6,306,663 B1 | 10/2001 | Kenten et al. |
| 6,309,663 B1 | 10/2001 | Patel et al. |
| 6,331,310 B1 | 12/2001 | Roser et al. |
| 6,371,939 B2 | 4/2002 | Bergens et al. |
| 6,495,164 B1 | 12/2002 | Ramstack et al. |
| 6,667,061 B2 | 12/2003 | Ramstack et al. |
| 6,676,958 B2 | 1/2004 | Gerber |
| 6,730,328 B2 | 5/2004 | Maskiewicz et al. |
| 7,005,421 B2 | 2/2006 | Gatti et al. |
| 7,163,704 B2 | 1/2007 | Zhang |
| 7,259,225 B2 | 8/2007 | Song et al. |
| 7,314,636 B2 | 1/2008 | Caseres et al. |
| 7,371,406 B2 | 5/2008 | Ramstack et al. |
| 7,396,841 B2 | 7/2008 | Doen et al. |
| 7,442,832 B2 | 10/2008 | Gentile et al. |

(Continued)

FOREIGN PATENT DOCUMENTS

| | | |
|---|---|---|
| WO | WO 91/16882 | 11/1991 |
| WO | WO 95/32730 | 12/1995 |

(Continued)

OTHER PUBLICATIONS

Glucagon—*Homo sapiens*, from http://www.ncbi.nlm.nih.gov/protein/AAH05278.1, pp. 1-2, accessed May 12, 2015.*
Surfactant Overview—Curosurf, from http://curosurf.com/conventional-treatment-strategies/surfactant-overview/, pp. 1-4, accessed May 12, 2015.*
Naturally-occurring amino acids, from http://www.benjamin-mills.com/chemistry/amino-acids.htm, pp. 1-4, accessed May 12, 2015.*
Water, from http://www.biology-online.org/dictionary/Water, pp. 1-3, accessed Apr. 24, 2014.*

(Continued)

*Primary Examiner* — Julie Ha
*Assistant Examiner* — Li Ni Komatsu
(74) *Attorney, Agent, or Firm* — Sheridan Ross P.C.

(57) ABSTRACT

The delivery of biopharmaceutical and other therapeutic agents parenterally to an animal via a minimally invasive, low pain administration is provided. The agents are delivered to the patient via, e.g., the epidermal, dermal, or subcutaneous layer of the skin in a concentrated form of injectable glucagon that is dissolved in a pharmaceutically acceptable carrier.

13 Claims, 9 Drawing Sheets

(56) References Cited

U.S. PATENT DOCUMENTS

| | | |
|---|---|---|
| 7,498,312 B2 | 3/2009 | Cohen et al. |
| 7,582,311 B1 | 9/2009 | Cleland et al. |
| 7,604,822 B2 | 10/2009 | Ionascu |
| 7,651,703 B2 | 1/2010 | Cleland et al. |
| 7,915,229 B2 | 3/2011 | Cohen et al. |
| 2003/0026844 A1 | 2/2003 | Lee et al. |
| 2003/0119825 A1 | 6/2003 | Folger et al. |
| 2003/0170289 A1 | 9/2003 | Chen et al. |
| 2003/0191157 A1 | 10/2003 | Doen et al. |
| 2004/0142043 A1 | 7/2004 | Maeda et al. |
| 2004/0176341 A1 | 9/2004 | Chou et al. |
| 2005/0019436 A1 | 1/2005 | Burch et al. |
| 2005/0069591 A1 | 3/2005 | Bernstein et al. |
| 2006/0160823 A1 | 7/2006 | Witchey-Lakshmanan et al. |
| 2006/0211982 A1 | 9/2006 | Prestrelski et al. |
| 2007/0196416 A1 | 8/2007 | Li et al. |
| 2008/0096967 A1 | 4/2008 | Lopez et al. |
| 2008/0132493 A1 | 6/2008 | Folger et al. |
| 2008/0160067 A1 | 7/2008 | Boeckh et al. |
| 2008/0220069 A1 | 9/2008 | Allison |
| 2008/0226689 A1 | 9/2008 | Berry et al. |
| 2008/0260840 A1 | 10/2008 | Alessi et al. |
| 2008/0305161 A1 | 12/2008 | Shah et al. |
| 2009/0215883 A1 | 8/2009 | Bouzada et al. |
| 2010/0098735 A1 | 4/2010 | Jain et al. |
| 2011/0060310 A1 | 3/2011 | Prestrelski et al. |
| 2012/0046225 A1 | 2/2012 | Prestrelski et al. |

FOREIGN PATENT DOCUMENTS

| | | | |
|---|---|---|---|
| WO | WO 96/09814 | 4/1996 | |
| WO | WO 98/09613 | 3/1998 | |
| WO | WO 98/16250 | 4/1998 | |
| WO | WO 98/27963 | 7/1998 | |
| WO | WO 00/16829 | 3/2000 | |
| WO | WO 01/76682 | 10/2001 | |
| WO | WO 01/78687 | 10/2001 | |
| WO | WO 02/00137 | 1/2002 | |
| WO | WO 02/49660 | 6/2002 | |
| WO | WO 03/007782 | 1/2003 | |
| WO | WO 03/041684 | 5/2003 | |
| WO | WO 2004/037242 | 5/2004 | |
| WO | WO 2004/057939 | 7/2004 | |
| WO | WO 2004/057959 | 7/2004 | |
| WO | WO 2004/091666 | 10/2004 | |
| WO | WO 2004/098643 | 11/2004 | |
| WO | WO 2004/105790 A1 * | 12/2004 | ............ A61K 38/26 |
| WO | WO 2005/010079 | 2/2005 | |
| WO | WO 2006/031376 | 3/2006 | |
| WO | WO 2007/140312 | 12/2007 | |
| WO | WO 2008/030469 | 3/2008 | |
| WO | WO 2008/041245 | 4/2008 | |
| WO | WO 2008/098212 | 8/2008 | |
| WO | WO 2008/132224 | 11/2008 | |
| WO | WO 2009/045837 | 4/2009 | |
| WO | WO 2009/060473 | 5/2009 | |
| WO | WO 2010/018596 | 2/2010 | |

OTHER PUBLICATIONS

Glycerol, from http://www.naturalwellbeing.com/learning-center/Glycerol, pp. 1-3, accessed Apr. 24, 2014.*

Sources of Citric Acid, from http://www.healthguidance.org/entry/16126/1/Sources-of-Citric-Acid.html 5/, pp. 1-3, accessed May 12, 2015.*

Richards et al, Trehalose: a review of properties, history of use and human tolerance, and results of multiple safety studies, Food and Chemical Toxicology, 2002, 40, pp. 871-898.*

Izutsu, Therapeutic proteins, methods and protocols, Humana press, edited by C. Mark Smales and David C. James, 2005, pp. 287-292.*

Fotaki et al, Rationale for Selection of Dissolution Media: Three Case Studies, Dissolution Technologies, 2013, pp. 6-13.*

Definition of analog, from http://cancerweb.ncl.ac.uk/cgi-bin/omd?query=analog, pp. 1-5, accessed Jul. 7, 2005.

Buffer Reference Center, from http://www.sigmaaldrich.com/life-science/core-bioregaents/biological-buffers/learning-cent . . . , pp. 1-7, accessed Jul. 3, 2013.

Carpenter et al, Rationale design of stable lyophilized protein formulations: theory and practice. In "Rationale Design of stable protein formulations—theory and practice", J.F. Carpenter and M.C. Manning eds., Kluer Academic/Plenum publishers, New York, 2002, enclosed pp. 1-25.

DeLuca, patrick P., J. Vac. Sci. Technol., vol. 14, No. 1, Jan./Feb. 1977.

Encyclopedia of Pharmaceutical Technology, vol. 6, Suspensions, pp. 3597-3610, 2007.

Meyer, J.D. et al., "Preparation and in Vitro Characterization of Gentamycin-Impregnated Biodegradable Beads Suitable for Treatment of Osteomyelitis," Journal of Pharmaceutical Sciences, Sep. 1998, vol. 87, No. 9, pp. 1149-1154.

Williams, N.A., and G.P. Polli, Journal of Parenteral Science and Technology, vol. 38, No. 2, Mar./Apr. 1984.

European Search report for related European Application No. EP 12180169.0, mailed Oct. 25, 2012, 7 pages.

Official Action for U.S. Appl. No. 13/186,275, mailed Sep. 19, 2012 Restriction Requirement.

Official Action for U.S. Appl. No. 13/186,275, mailed Dec. 28, 2012.

Official Action for U.S. Appl. No. 13/186,275, mailed Aug. 22, 2013.

International Search Report for International (PCT) Patent Application No. PCT/US11/44576, mailed Dec. 14, 2011 3 pages.

International Preliminary Report on Patentability for International (PCT) Patent Application No. PCT/US2011/044576, mailed Jan. 31, 2013 7 pages.

* cited by examiner

STABLE GLUCAGON FORMULATIONS FOR THE TREATMENT OF HYPOGLYCEMIA

CROSS-REFERENCES TO RELATED APPLICATIONS

This application is a continuation of U.S. patent application Ser. No. 13/186,275, filed Jul. 19, 2011 and abandoned Apr. 22, 2014, which claims priority to and the benefit of U.S. Provisional Application No. 61/365,637, filed Jul. 19, 2010, expired Jul. 24, 2011, and entitled "Stable Glucagon Formulations for the Treatment of Hypoglycemia," the entire disclosures of which are herein incorporated by reference for all purposes.

STATEMENT AS TO RIGHTS TO INVENTIONS MADE UNDER FEDERALLY SPONSORED RESEARCH OR DEVELOPMENT

This invention was made with government support under grant number DK085809 awarded by The National Institutes of Health. The government has certain rights in the invention.

BACKGROUND OF THE INVENTION

Parenteral injection refers to the administration of drugs or vaccines via injection under or through one or more layers of skin or mucus membranes of an animal. Standard injections are given into the subcutaneous or intramuscular region of an animal, e.g., a human patient. These deep locations are targeted because the tissue expands more easily, relative to shallow dermal sites, to accommodate the 0.13 cc (ml) injection volumes required to deliver most therapeutic agents.

Generally, injections have been classified into different categories, including (1) solutions ready for injection; (2) dry, soluble products ready to be combined with a solvent just prior to being injected into a patient; (3) dry, insoluble products ready to be combined with a suitable injection medium prior to administration; (4) suspensions ready for injection; and (5) emulsions ready for injection. Such injectable formulations are administered by routes including intravenous, subcutaneous, intradermal, intramuscular, intraspinal, intrasistemal, and intrathecal. The nature of the therapeutic agent quickly determines the route of administration. However, the desired route of administration places constraints on the therapeutic formulation itself. For example, solutions for subcutaneous administration require strict attention to tonicity adjustment in order to avoid irritation to the nerves and tissue in the surrounding area of injection. Likewise, suspensions are not administered directly into the blood stream in view of the potential of insoluble particles blocking capillaries.

In comparison to other dosage forms and routes of administration, injectables possess certain advantages, including immediate physiological action (e.g., via intravenous injection), avoidance of intestinal absorption problems attended with many drugs, and the accurate administration of the desired dose into the blood stream of a patient. However, one of the disadvantages of injectables is the pain and discomfort present at the site of administration associated with certain pharmaceutically active agents, as well as the trauma of having a needle inserted under the skin or into a vein. Clearly, there can be some degree of discomfort for the patient with each injection that is administered.

Biopharmaceutical agents are typically reconstituted into sterile solutions for injection into the subcutaneous or intramuscular space using a large gauge needle, e.g., in the range 18-30 gauge. Pain is caused by the depth of the penetration of the needle, the size "gauge" of the needle, the large volume of injection, and the diffusion of drug away from the site of injection, among other things. In addition to problems with administration of injectables due to pain associated with the same, there are other draw backs of current practices with respect to injections. For example, many protein and sustained release drugs require reconstitution immediately prior to administration. Dosing of drugs can be inflexible and inaccurate. Further, many formulations need to be refrigerated in order to protect the drugs from degrading hydrolysis reactions. Further, present administration systems are wasteful in that the injection device retains a significant amount of the drug product. Further, to effect delivery of the necessary dose required, an injectable formulation typically must be concentrated and stabilized. Standard injections are given in the liquid form. Products that are sold as liquids or as lyophilized powders require reconstitution in an aqueous carrier prior to injection. Many therapeutic protein and vaccine products are produced in a dry, solid form to promote stability while on the shelf. These formulations are diluted prior to injection in sterile water, phosphate buffer solution, or isotonic saline.

PCT Publication No. WO 2004/057959, which is hereby incorporated by reference to the same extent as though fully replicated herein, describes an auto-injection device that can be used to administer ultraconcentrated biopharmaceutical agents by injection in the form of a paste or suspension. The relatively low volume of these formulations facilitates a minimally invasive, low-pain administration by injection into the epidermal, dermal or subcutaneous layer of the skin. While this constitutes a significant advance in the art, the paste suspensions may require various surfactants and other ingredients, for example, antioxidants to stabilize the biopharmaceutical agents and surfactants to improve the injectable nature of the formulation. Other auto-injection devices include auto-injectors as described, for example, in U.S. Pat. No. 5,092,843, which issued to Monroe et al. These devices deliver biopharmaceutical agents by injection in that is assisted by the power stroke of a piston.

Despite the advances that have been made with injectables, there is needed in the art simplified methods and formulations that provide dosing of therapeutic peptides and other biopharmaceuticals in a concentrated dose via intracutaneous injection into the epidermal, dermal or subcutaneous layer of the skin. Further, it would be beneficial if such formulations were provided in a stabilized platform that does not require reconstitution or refrigeration. Still further, it would be beneficial if such formulations could be administered in a manner that substantially avoids pain associated with the injection of such formulations.

SUMMARY OF THE INVENTION

The present invention overcome the problems outlined above and advances the art by providing stable glucagon formulations for parenteral injection that can be formulated as solutions, suspensions or pastes. Importantly, the injectable formulations of the present invention advantageously promote uniform delivery of glucagon and provide additional shelf stability against aggregation, oxidation and hydrolysis related degradation pathways. In fact, the stable glucagon compositions of the present invention have both increased chemical stability and physical stability. For instance, a stable glucagon composition, prepared by drying glucagon or a glucagon analog with a glycine buffer and trehalose, has less than 2% chemical degradation and less than 3% physical degradation after storage at 60° C. for two weeks.

As such, in one embodiment, the present invention provides a stable glucagon composition, the composition may comprise, consist or consist essentially of: glucagon or a glucagon analog that has been dried with a carbohydrate and a buffer having a pH of about 2.0 to about 3.5. In one embodiment, the glucagon or glucagon analog, the buffer and the carbohydrate are dried using standard drying techniques, including spray-drying, lyophilization or freeze-drying, and dessication. Once dried, the stable glucagon composition (i.e., the dried glucagon powder) can be reconstituted or mixed with a pharmaceutically acceptable carrier or diluent. In one embodiment, the pharmaceutically acceptable carrier can be an aqueous carrier, and the resulting pharmaceutical formulation is a solution. In another embodiment, the stable glucagon formulation can be mixed or combined with a pharmaceutically acceptable carrier at a concentration such that the resulting pharmaceutical formulation is a suspension. In yet another embodiment, the stable glucagon formulation can be mixed or combined with a pharmaceutically acceptable carrier at a concentration such that the resulting pharmaceutical formulation is a paste. In one embodiment, the pharmaceutically acceptable carrier is an aqueous carrier. In other embodiments, the pharmaceutically acceptable carrier is a non-aqueous carrier including, but are not limited to, lipids, aryl benzonates, alkyl benzonates and triacetin. In presently preferred embodiments, the non-aqueous carrier is triacetin, benzyl benzoate, miglyol, palm oil or mineral oil. Generally, the final concentration of glucagon in the solution, suspension or paste can range, for example, from about 0.1% up to about 70% (w/w), depending on the nature of the glucagon formulation and the pharmaceutically acceptable carrier or diluent employed in the pharmaceutical formulation.

In the stable glucagon compositions of the present invention, the buffer typically has a pH ranging from about 2.0 to about 3.5. In a preferred embodiment, the buffer has a pH of about 3.0. Suitable buffers include, but are not limited to, glycine buffers, citrate buffers and phosphate buffers. In a preferred embodiment, the buffer is a glycine buffer. In another preferred embodiment, the buffer is a citrate buffer. As noted, the glucagon or glucagon analog is dried with the buffer, which helps to protect against the chemical degradation of the glucagon, and a carbohydrate, which helps to preserve the α-helix of glucagon. Carbohydrates suitable for use in the compositions of the present invention include, for example, sugars and starches. Suitable sugars and starches include, but are not limited to, trehalose, hydroxyethyl starch (HES), dextran and mixtures thereof. In a preferred embodiment, the carbohydrate is trehalose. In another preferred embodiment, the carbohydrate is HES. In yet another preferred embodiment, the carbohydrate is a mixture of trehalose and HES, Typically, the ratio of [carbohydrate] to [glucagon] is about 1:1 to about 3:1, and preferably about 2:1. Once mixed, the glucagon, carbohydrate and buffer mixture, which may optionally include other additional components, such as polysorbate 20 (i.e., Tween® 20), is freeze-dried to a dried powder using techniques known to and used by those of skill in the art.

In preferred embodiments of the present invention, the stable glucagon compositions or pharmaceutical formulations made from such stable glucagon compositions can further include a surfactant that protects the glucagon peptide from physical damage (such as polysorbate 20 or polysorbate 80).

In some embodiments, the stable glucagon compositions or pharmaceutical formulations made from such stable glucagon compositions can further comprise at least one stabilizing excipient, additive or solvent. In some embodiments, the stabilizing excipient is capable of stabilizing the conformation of the glucagon or glucagon analog or glucagon mimetic.

In some embodiments, the stable glucagon compositions or pharmaceutical formulations made from such stable glucagon compositions can further comprise at least one non-aqueous protic solvent. Examples of non-aqueous protic solvents include, but are not limited to, polyethylene glycol (PEG), propylene glycol (PG), polyvinylpyrrolidone (PVP), methoxypropylene glycol (MPEG), glycerol, glycofurol, and mixtures thereof.

In some embodiments, the stable glucagon compositions or pharmaceutical formulations made from such stable glucagon compositions further comprise an antioxidant. Suitable antioxidants include, but are not limited to, ascorbic acid, cysteine, methionine, monothioglycerol, sodium thiosulphate, sulfites, BHT, BHA, ascorbyl palmitate, propyl gallate, and Vitamin E.

In some, embodiments, the stable glucagon compositions or pharmaceutical formulations made from such stable glucagon compositions further comprise a chelator. Examples of chelators include, but are not limited to, EDTA, tartaric acid and salts thereof, glycerin, and citric acid and salts thereof.

In some embodiments, the stable pharmaceutical formulation further comprises a preservative. Suitable preservatives include, for example, benzyl alcohols, methyl parabens and propyl parabens.

In still other aspects, viscosity of the glucagon formulations is suitably from about 0.25 cP to about 1,000,000 cP. The pH is preferably at or below the pI of glucagon or glucagon analog. Typically, the pH ranges from about 2.0 to about 3.5. In preferred embodiments, the pH is about 3.0.

"Effective doses of the glucagon" are those doses that deliver a medically effective amount of glucagon. The formulations to deliver these doses contain glucagon or a glucagon analog (collectively "glucagon") that is present at a concentration from about 0.1 mg/ml up to the solubility limit of the glucagon peptide in the formulation. This concentration is preferably from about 1 mg/ml to about 100 mg/ml.

In anther aspect, the present invention provides a method for treating a disease, condition or disorder that may be treated, alleviated or prevented by administering to a subject a pharmaceutical formulation as described herein, in an amount effective to treat, alleviate or prevent the disease, condition or disorder. In some embodiments, the disease, condition or disorder comprises hypoglycemia or severe hypoglycemia.

In yet another aspect, the present invention provides the use of a pharmaceutical formulation as described herein, for the treatment of a disease, condition or disorder that may be treated, alleviated or prevented by administering a glucagon peptide. In some embodiments, the disease, condition or disorder comprises hypoglycemia or severe hypoglycemia.

In some embodiments, the administration is parenteral administration. In some embodiments, the administration is continuous administration. In some embodiments, the administration is continuous for a period ranging from about 1 month to about 6 months. In some embodiments, the administration is accomplished via use of an implantable or attachable pump drug delivery device. In other embodiments, the administration is accomplished via use of a pen injection device.

Importantly, the present invention provides injectable formulations that can be administered to deliver glucagon into the epidermal, dermal or subcutaneous layer of an animal to effect pain-free or substantially pain-free administration of the glucagon.

The present invention also provides concentrated injectable formulations containing an effective amount of glucagon that may be injected into the epidermal, dermal or subcutaneous layer of skin of an animal.

The present invention further provides methods of treating mammals, e.g., human patients, utilizing the injectable formulation of glucagon described herein.

In certain embodiments, the present invention provides a stable glucagon composition, the stable glucagon composition may comprise, consist essentially of or consist of a mixture of a glucagon or a glucagon analog that has been dried with a carbohydrate and a buffer having a pH of about 2.0 to about 3.5, and a pharmaceutically acceptable carrier. In one embodiment, the pharmaceutically carrier is an aqueous carrier. In another embodiment, the pharmaceutically acceptable carrier is a non-aqueous carrier selected from the group consisting of lipids, aryl benzonates, alkyl benzonates and triacetin.

A method for treating hypoglycemia in a subject in need thereof, the method comprising administering to the subject a pharmaceutical formulation of the present invention in an amount effective to treat hypoglycemia. In one embodiment, the pharmaceutical formulation is a stable glucagon composition that may comprise, consist essentially of or consist of a mixture of a glucagon or a glucagon analog that has been dried with a carbohydrate and a buffer having a pH of about 2.0 to about 3.5, and a pharmaceutically acceptable carrier. In one embodiment, the pharmaceutically carrier is an aqueous carrier. In another embodiment, the pharmaceutically acceptable carrier is a non-aqueous carrier selected from the group consisting of lipids, aryl benzonates, alkyl benzonates and triacetin.

Other objects, features, and advantages of the present invention will be apparent to one of skill in the art from the following detailed description and claims.

DETAILED DESCRIPTION OF THE INVENTION

I. Definitions

Figure 1A:
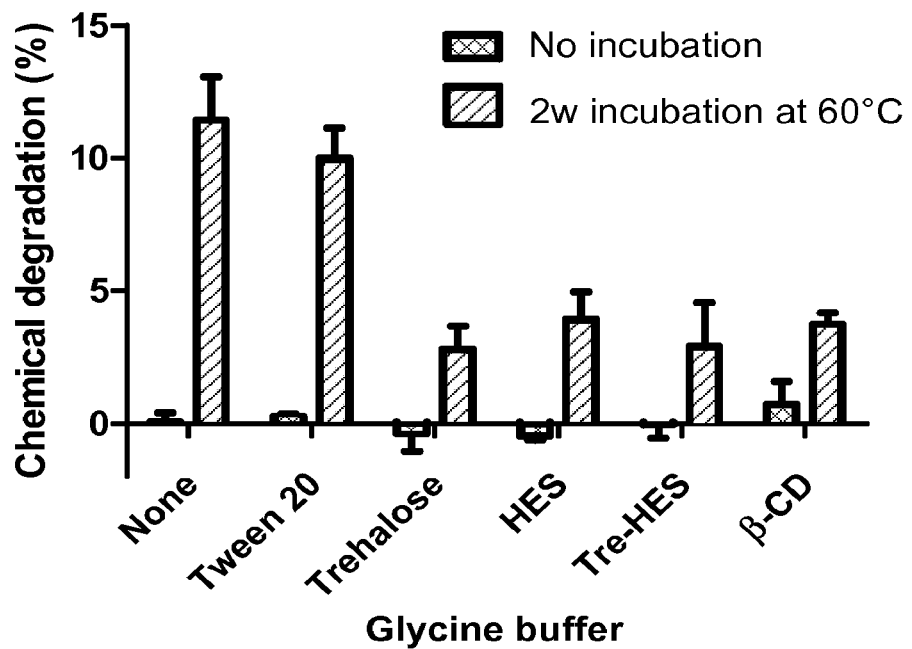
FIG. 1 illustrates the chemical degradation (%) of glucagon in different formulations following freeze-drying and incubation at 60° C. for 2 weeks as determined by RP-HPLC: (A) Glycine buffer; (B) Phosphate buffer; and (C) Citrate buffer. The values are the mean±SD from three independent experiments.

For purposes of the present disclosure, the following terms have the following meanings:

The term "therapeutic agent" encompasses peptide compounds together with pharmaceutically acceptable salts thereof. Useful salts are known to those skilled in the art and include salts with inorganic acids, organic acids, inorganic bases, or organic bases. Therapeutic agents useful in the present invention are those glucagon peptides that affects a desired, beneficial, and often pharmacological, effect upon administration to a human or an animal, whether alone or in combination with other pharmaceutical excipients or inert ingredients.

The term in "intracutaneous" encompasses administration into the epidermal, dermal or subcutaneous skin layer.

The term "pharmaceutically acceptable carrier" means a pharmaceutically acceptable solvent, suspending agent or vehicle for delivering a compound of the present invention to the animal or human. The carrier may be liquid, semisolid or solid.

The term "pharmaceutically acceptable" ingredient, diluent, excipient or component is one that is suitable for use with humans and/or animals without undue adverse side effects (such as toxicity, irritation, and allergic response) commensurate with a reasonable benefit/risk ratio.

The term "chemical stability" means that with respect to the therapeutic agent, an acceptable percentage of degradation products produced by chemical pathways such as oxidation or hydrolysis is formed. In particular, a formulation is considered chemically stable if no more than about 20% breakdown products are formed after one year of storage at the intended storage temperature of the product (e.g., room temperature); or storage of the product at 30° C./60% relative humidity for one year; or storage of the product at 40° C./75% relative humidity for one month, and preferably three months.

The term "physical stability" means that with respect to the therapeutic agent, an acceptable percentage of aggregates (e.g., dimers, trimers and larger forms) is formed. In particular, a formulation is considered physically stable if no more that about 15% aggregates are formed after one year of storage at the intended storage temperature of the product (e.g., room temperature); or storage of the product at 30°

C./60% relative humidity for one year; or storage of the product at 40° C./75% relative humidity for one month, and preferably three months.

The term "stable formulation" means that at least about 65% chemically and physically stable therapeutic agent remains after two months of storage at room temperature. Particularly preferred formulations are those which retain at least about 80% chemically and physically stable therapeutic agent under these conditions. Especially preferred stable formulations are those which do not exhibit degradation after sterilizing irradiation (e.g., gamma, beta or electron beam).

The term "bioavailability" is defined for purposes of the present invention as the extent to which the therapeutic agent, such as a peptide compound, is absorbed from the formulation.

The term "systemic" means, with respect to delivery or administration of a therapeutic agent, such as a peptide compound, to a subject, that therapeutic agent is detectable at a biologically-significant level in the blood plasma of the subject.

The term "controlled-release" is defined for purposes of the present invention as the release of the therapeutic agent at such a rate that blood (e.g., plasma) concentrations are maintained within the therapeutic range, but below toxic concentrations over a period of time of about one hour or longer, preferably 12 hours or longer.

The term "parenteral injection" refers to the administration of therapeutic agents, such as peptide compounds, via injection under or through one or more layers of skin or mucus membranes of an animal, such as a human. Standard parenteral injections are given into the subcutaneous or intramuscular region of an animal, e.g., a human patient. These deep locations are targeted because the tissue expands more easily, relative to shallow dermal sites, to accommodate the 0.1-3.0 cc (mL) injection volumes required to deliver most therapeutic agents.

II. Overview and Preferred Embodiments

Proteins can degrade via a number of mechanisms, including deamidation, oxidation, hydrolysis, disulfide interchange, and racemization. Further, water acts as a plasticizer, which facilitates unfolding of protein molecules and irreversible molecular aggregation. Therefore, in order to provide a protein formulation that is stable over time at ambient or physiological temperatures, a non-aqueous or substantially non-aqueous protein formulation is generally required.

Reduction of aqueous protein formulations to dry powdered formulations is one way to increase the stability of pharmaceutical protein formulations. For example, protein formulations can be dried using various techniques, including spray-drying, lyophilization or freeze-drying, and dessication. The dry powder protein formulations achieved by such techniques exhibit significantly increased stability over time at ambient or even physiological temperatures. However, where a flowable protein formulation is required, such as in an implantable delivery device, dry powder protein formulations alone are of limited use.

The pharmaceutical formulations of the present invention comprising the stable glucagon composition and a pharmaceutically acceptable carrier or diluent are stable, flowable protein formulations. Advantageously, such pharmaceutical formulations are stable at elevated temperatures for long periods of time.

Standard injection volumes associated with most therapeutic injections are too large to avoid pain in the epidermal, dermal, or subcutaneous layer. In order to accomplish a low-pain or pain-free injection (or administration) of a therapeutic agent into an animal (e.g., a human patient), a much smaller injection volume is required. Standard injections are given into the subcutaneous or intramuscular region of a patient. These deep locations are targeted because the tissue expands more easily, relative to shallow dermal sites, to accommodate the 0.1-1.0 ml injection volumes required by most therapeutic injectables. Injection of large viscous volumes tends to cause more pain than small dilute volumes. However, viscous medications have not been administered intracutaneously in the past because a large lumen needle is required. Such needles cannot be used for intracutaneous administration. Additionally, liquid formulations must be injected slowly when done intracutaneously to avoid tissue damage and volumes greater than 0.5 ml cannot be administered intracutaneously.

The injectable formulations of the present disclosure contain the necessary delivered dose of therapeutic agent (e.g., a glucagon dose that is required for drug therapy), and are preferably low volume, i.e., the injectable formulation containing a therapeutic dose of glucagon has a volume of at least about 1 microliters (the lower limit being a function of the filling equipment), more preferably from about 1 microliter to about 250 microliters. This is accomplished in certain preferred embodiments by drying the of glucagon with a carbohydrate and a buffer having a pH of about 2.0 to about 3.5, and then reconstituting the glucagon dry powder with a pharmaceutically acceptable carrier or diluent for injection in accordance with the invention. In certain embodiments, the low volume of injectable dose is accomplished by concentrating the dose of glucagon in a stable form with the carbohydrate and the buffer, along with any other optional components.

In certain embodiments, the low volume formulations of the present invention are administrable without being diluted, or reconstituted, or refrigerated. In such embodiments, therapeutic dosages of glucagon are obtained by mixing the dried glucagon powder with a pharmaceutically acceptable diluent. Suitable diluents include, but are not limited to, lipids, aryl benzoates, alkyl benzoates and triacetin. Particularly preferred diluents include triacetin, benzyl benzoate, miglyol, palm oil and mineral oil.

In certain preferred embodiments of the present invention, the therapeutic agent is concentrated using the same particle preparation processes (e.g., spray drying, lyophilization, etc.) techniques routinely employed by the pharmaceutical industry to prepare formulations for injection. However, as noted herein, in certain preferred embodiments, the pharmaceutical formulations of the present invention are is injected or otherwise administered into the animal (e.g., human patient) without diluting the formulations prior to injection as required by reconstitution products.

The pharmaceutical formulations of the present invention can be placed into an injection device and are presented in the device so that the formulations are able to flow out of the needle upon actuation of an injection device, such as an auto-injector, in order to deliver the glucagon for the treatment of, for example, hypoglycemia.

The injectable formulations described herein advantageously promote uniform delivery of glucagon and provide additional shelf stability against aggregation, oxidation and hydrolysis related degradation pathways.

In certain preferred embodiments, the injectable formulations preserve glucagon in a stable form for a prolonged period of time, e.g., sufficient to provide a desired shelf-life of the formulations without unacceptable levels of chemical and/or physical degradation of the therapeutic agent, i.e., glucagon, prior to use. In a preferred embodiment, a desired property of the injectable formulations is that they be non-aqueous and nonreactive with respect to the glucagon. In such embodiments, it is possible to store the injectable formulations directly in the injection device itself.

In certain embodiments, surfactants can be incorporated into the pharmaceutical formulations of the present invention in order, e.g., to aid in the flow of the formulation through the needle of the injection device and/or to aid in the dissolution of the solid, i.e., dry powder, therapeutic agent. Surfactants that can be used in the present invention generally include pharmaceutically acceptable anionic surfactants, cationic surfactants, amphoteric (amphipathic/amphophilic) surfactants, and nonionic surfactants.

Suitable pharmaceutically acceptable anionic surfactants include, for example, monovalent alkyl carboxylates, acyl lactylates, alkyl ether carboxylates, N-acyl sarcosinates, polyvalent alkyl carbonates, N-acyl glutamates, fatty acid-polypeptide condensates, sulfuric acid esters, alkyl sulfates (including sodium lauryl sulfate (SLS)), ethoxylated alkyl sulfates, ester linked sulfonates, alpha olefin sulfonates, and phosphated ethoxylated alcohols.

Suitable pharmaceutically acceptable cationic surfactants include, for example, monoalkyl quaternary ammonium salts, dialkyl quaternary ammonium compounds, amidoamines, and aminimides.

Suitable pharmaceutically acceptable amphoteric (amphipathic/amphophilic) surfactants, include, for example, N-substituted alkyl amides, N-alkyl betaines, sulfobetaines, and N-alkyl beta-aminoproprionates.

Pharmaceutically acceptable wetting (solubilizing) agents suitable for use in the pharmaceutical formulations of the present invention, include pharmaceutically acceptable non-ionic surfactants such as, for example, polyoxyethylene compounds, ethoxylated alcohols, ethoxylated esters, ethoxylated amides, polyoxypropylene compounds, propoxylated alcohols, ethoxylated/propoxylated block polymers, and propoxylated esters, alkanolamides, amine oxides, fatty acid esters of polyhydric alcohols, ethylene glycol esters, diethylene glycol esters, propylene glycol esters, glyceryl esters, polyglyceryl fatty acid esters, sorbitan esters, sucrose esters, and glucose (dextrose) esters.

In certain embodiments, preferred surfactants include, e.g., hexadecylamine, octadecyl amino acid esters, octadecylamine, lysolecithin, dimethyl-dioctadecylammonium bromide, N,N-dicoctadecyl-N'—N'bis(2-hydroxyethyl-propane diamine), methoxyhexadecylglycerol, and pluronic polyols (e.g., a desirable quantity of an alkylene polyoxide (sold by BASF under the name of Pluronic PE 4300). The particular surfactant should be chosen with respect to the therapeutic agent used in the formulation, keeping in mind compatibility and ability to dissolve or wet the therapeutic agent.

Similarly, in those embodiments where the pharmaceutical formulation is a paste, any liquid that enhances the injectability of a solid through a needle should be considered a viable aspect of this invention. Thus, in certain embodiments, the paste formulation for injection includes one or more injectability enhancing agents. Examples of such agents include, but are not limited to, silicon oil, waxes, oils, lubricants, greases, and petroleum jelly.

The pharmaceutical formulations of the present invention can include other pharmaceutically acceptable ingredients or excipients useful for injection, including but not limited to, additional pharmaceutically acceptable excipients. Such additional ingredients to be included in the formulation preferably possess the necessary rheological properties to allow for displacement of the suspension or paste under reasonable pressures (i.e., do not interfere with the injectability of the formulation). As a general rule, thumb pressure is the lower end (e.g., a few newtons) of the pressure that can be generated with a syringe. Such additional ingredients can include e.g., antioxidizing agents, such as sodium bisulfite, sodium sulfite, ascorbic acid or methionine, either alone or combined, with other suitable stabilizing agents. Also used are citric acid salts thereof, or sodium EDTA; preservatives, such as benzalkonium chloride, methyl- or propyl-paraben, or chlorobutanol, potassium sorbate, sorbic acid, sulfur dioxide, propyl gallate, the parabens, ethyl vanillin, glycerin, phenol, and parachlorophenol.

In certain embodiments of the present invention can further include polymers that are preferably biodegradable and/or biocompatible. Such polymers include, but are not limited to, polylactides, polyglycolides, polycaprolactones, polyanhydrides, polyamines, polyurethanes, polyesteramides, polyorthoesters, polydioxanones, polyacetals, polyketals, polycarbonates, polyorthocarbonates, polyphosphazenes, succinates, poly(malic acid), poly(amino acids), polyvinylpyrrolidone, polyethylene glycol, polyhydroxycellulose, chitin, chitosan, and copolymers, terpolymers and mixtures thereof.

Presently preferred polymers are polylactides, polyglycolides, and copolymers of lactic acid and glycolic acid. These polymers may include amounts of other comonomers that do not substantially affect the advantageous results which can be achieved in accordance with the present invention. As used herein, the term "lactic acid" includes the isomers L-lactic acid, D-lactic acid, DL-lactic acid and lactide while the term "glycolic acid" includes glycolide. Most preferred are poly(lactide-co-glycolide) copolymers, commonly referred to as PLGA. The polymer may have a monomer ratio of lactic acid/glycolic acid of from about 100:0 to about 15:85, preferably from about 60:40 to about 75:25 and an especially useful copolymer has a monomer ratio of lactic acid/glycolic acid of about 50:50.

Any suitable dosage of glucagon can be administered in the methods of the present invention. The dosage administered will, of course, vary depending upon known factors, such as the pharmacodynamic characteristics of the particular compound, salt, or combination; the age, health, or weight of the subject; the nature and extent of symptoms; the metabolic characteristics of the drug and patient, the kind of concurrent treatment; the frequency of treatment; or the effect desired.

In preferred embodiments of the present invention, the glucagon is dried into a nonstructured, densified state and then combined or mixed with a pharmaceutically acceptable carrier or diluent to form a fluidized solution, suspension or paste of minimal injection volume. In certain preferred embodiments, the dried therapeutic agent is processed in order to decrease its particle size by any pharmaceutically acceptable manner known to those skilled in the art. Various methods of particle size manipulation and/or reduction can be utilized in order to prepare the therapeutic formulations useful in the present invention. Such particle size reduction procedures include, but are not limited to, comminuting processes (cutting, chopping, crushing, grinding, milling, micronizing, nanosizing, freeze drying, spray-freeze-drying, trituration, and microfluidization).

Spray drying techniques are well known to those skilled in the art. Spray drying includes the steps of atomization of a solution containing one or more solid (e.g., therapeutic agent) via a nozzle spinning disk, or other device, followed by evaporation of the solvent from the droplets. The nature of the powder that results the function of several variables including the initial solute concentration, size distribution of droplets produced and the rate of solute removal. The particles produced may comprise aggregates of primary particles that consist of crystals and/or amorphous solids depending on the rate and conditions of solvent removal.

A spray-drying process for preparing ultra-fine powders of biological macromolecules such as proteins, oligopeptides, high molecular weight polysaccharides, and nucleic acids is described in U.S. Pat. No. 6,051,256. Freeze-drying procedures are well known in the art, and described, for example, in U.S. Pat. No. 4,608,764 and U.S. Pat. No. 4,848,094. Spray-freeze-drying processes are described, e.g., in U.S. Pat. No. 5,208,998. Other spray-drying techniques are described, for example, in U.S. Pat. Nos. 6,253,463; 6,001,336; 5,260,306; and International Patent Publication Nos. WO 91/16882 and WO 96/09814.

Lyophilization techniques are well known to those skilled in the art. Basically, lyophilization is a dehydration technique that takes place while a product is in a frozen state (ice sublimation under a vacuum) and under a vacuum (drying by gentle heating). These conditions stabilize the product, and minimize oxidation and other degradative processes. The conditions of freeze drying permit running the process at low temperatures, thereby preserving thermally labile products. Steps in freeze drying typically include pretreatment, freezing, primary drying and secondary drying. Pretreatment includes any method of treating the product prior to freezing. This may include concentrating the product, formulation revision (i.e., addition of components to increase stability and/or improve processing), decreasing a high vapor pressure solvent or increasing the surface area. Methods of pretreatment include: freeze concentration, solution phase concentration, and formulating specifically to preserve product appearance or to provide lyoprotection for reactive products, and are described, e.g., in U.S. Pat. No. 6,199,297. Standard lyophilization conditions, are described, e.g., in U.S. Pat. No. 5,031,336, in "Freeze Drying of Pharmaceuticals" (DeLuca, Patrick P., J. Vac. Sci. Technol., Vol. 14, No. 1, January/February 1977); and in "The Lyophilization of Pharmaceuticals: A Literature Review" (Williams, N. A., and G. P. Polli, Journal of Parenteral Science and Technology, Vol. 38, No. 2, March/April 1984).

In certain preferred embodiments, the lyophilization cycle is partially performed above the glass transition temperature (Tg) of the therapeutic agent formulation to induce a collapse of the mass to form a dense cake containing residue moisture. In contrast, in typical prior art methods, the primary drug lyophilization is carried out below the glass transition temperature in order to avoid a collapse in order to achieve a complete drying of the particles. The residual moisture contained in dense cake formed by this preferred method is removed by placing the collapsed cake into solution of semi-(or minimal aqueously miscible, pharmaceutically acceptable carrier. The carrier then can be removed or used as the fluidity carrier for injection of the therapeutic formulation.

In certain preferred embodiments where the therapeutic agent comprises a bioactive agent (e.g., one or more proteins, peptides, polypeptides, etc.), a carrier compound comprising a stabilizing polyol is included in the formulation which is to be dried. Such formulations and materials are described for example in U.S. Pat. Nos. 6,290,991 and 6,331,310, both of which are hereby incorporated by reference.

Once the glucagon, the carbohydrate and the buffer (as well as any other optional components, additives or excipients) are dried to a dry powder as set forth herein, they are then fluidized for injection by mixing with a pharmaceutically acceptable carrier or diluent. As noted herein, the formulations of the present invention can contain additional ingredients, as described above, to impart further stability and improve rheological properties and facilitate administration. The pharmaceutically acceptable carrier is preferably a non-aqueous or a semi-aqueous carrier in order to promote stability and aid in complete injection of the dose. In preferred embodiments, the term "fluidized for injection" means that the glucagon content of the dose for injection is from about 1 to about 99 percent, by weight, and more preferably from about 50 to about 85% by weight.

In contrast to standard subcutaneous injections, where the injection volumes range from 0.3-1.2 ml (equivalent to 300-1200 microliters), the injection volumes of the pharmaceutical formulations of the present invention range from about 0.1 to about 10 microliters. This is accomplished via the use of a dry peptide powder that allows for a low-volume, shallow injection through a fine needle. In preferred embodiments, the needle is 27 to 30 gauge, and has a inner diameter of about 0.33 mm. The injection is preferably made to a depth in the skin from about 300 microns to about 500 microns.

In one preferred embodiment, glucagon and a minimal amount of pharmaceutically acceptable excipients are lyophilized to form an amorphous (nonstructured) solid mass having a low volume (per unit dose). These formulations minimize the amount of agents needed to stabilize the protein. In contrast, typical lyophilization solutions comprise, in addition to the protein, carbohydrate, buffers, solution stabilizers, bulking agents, dissolution agents, and nonspecific binding agents. Bulking agents required for particle formulation, process metering and flowability are not needed in the formulations of the present invention. Similarly, solution stabilizers are not required. By eliminating bulking agents and solution stabilizers as well as reducing the amounts of other ingredients needed to prepare a suitable injection media for glucagon, the proposed injection volume can be greatly reduced as compared to current volumes for injection of proteins. In certain embodiments, the pure protein may be used alone, if stable, or with a minimal amount of carbohydrate/stabilizer and buffer, e.g., approx. 0-3% by weight. The more concentrated the protein when dry (e.g., from about 25 to about 60% protein solids), the less carbohydrate is needed.

In certain preferred embodiments, a polymeric element is incorporated into the non-aqueous or semi-aqueous carrier in order to add structure to the liquid. By adding such polymers, e.g., polylactic acids, polyglycolic acids, polylactic-co-glycolic acids, polyanhydrides, polyorthoesters, and combinations thereof, two unique rheological properties are provided to the injectable formulations of the present invention. First, with respect to shear which occurs as the formulation is injected from the injection device, as the mass begins to flow out of the needle the carrier viscosity reduces the injection force required to force all of the injection dose out of the needle. Second, the injection of a polymer in addition to promoting drug flow prevents settling of the solid drug within the carrier. These properties (shear thinning liquid and rest shear) combine to accomplish dose proportionality.

III. Formulation Examples

The present invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1: Preparation of Glucagon Solutions for Use in Freeze-Drying

Various solutions were prepared to contain glucagon at a concentration of 10 mg/mL. The solutions contained, alternatively, glycine, citrate or phosphate at 5 mM, generally providing a buffer establishing pH of 3. The solution also contained a sugars, alone or in combination, in amounts equal to the w/v amount of glucagon (1:1) or at 200% (2:1) of the amount of glucagon. The sugars were trehalose, HES, and β-cyclodextrin β-CD. Some solutions also contained Tween 20 at 0.10% w/v as a surfactant. The various formulations mixed to substantial homogeneity in amounts as described in Table 1 below:

TABLE 1

Glucagon mixtures for subsequent lyophilization.

| Formulation | Glucagon (mg/ml) | Gycine Buffer (mM) | Citrate Buffer (mM) | Phosphate Buffer (mM) | Trehalose (mg/ml) | HES (mg/ml) | β-CD (mg/ml) | Tween-20 (mg/ml) |
|---|---|---|---|---|---|---|---|---|
| 1 | 5 | 5 | 0 | 0 | 0 | 0 | 0 | 0 |
| 2 | 5 | 5 | 0 | 0 | 0 | 0 | 0 | 0.01 |
| 3 | 5 | 5 | 0 | 0 | 10 | 0 | 0 | 0 |
| 4 | 5 | 5 | 0 | 0 | 0 | 10 | 0 | 0 |
| 5 | 5 | 5 | 0 | 0 | 5 | 5 | 0 | 0 |
| 6 | 5 | 5 | 0 | 0 | 0 | 0 | 10 | 0 |
| 7 | 5 | 0 | 5 | 0 | 0 | 0 | 0 | 0 |
| 8 | 5 | 0 | 5 | 0 | 0 | 0 | 0 | 0.01 |
| 9 | 5 | 0 | 5 | 0 | 10 | 0 | 0 | 0 |
| 10 | 5 | 0 | 5 | 0 | 0 | 10 | 0 | 0 |
| 11 | 5 | 0 | 5 | 0 | 5 | 5 | 0 | 0 |
| 12 | 5 | 0 | 5 | 0 | 0 | 0 | 10 | 0 |
| 13 | 5 | 0 | 0 | 5 | 0 | 0 | 0 | 0 |
| 14 | 5 | 0 | 0 | 5 | 0 | 0 | 0 | 0.01 |
| 15 | 5 | 0 | 0 | 5 | 10 | 0 | 0 | 0 |
| 16 | 5 | 0 | 0 | 5 | 0 | 10 | 0 | 0 |
| 17 | 5 | 0 | 0 | 5 | 5 | 5 | 0 | 0 |
| 18 | 5 | 0 | 0 | 5 | 0 | 0 | 10 | 0 |
| 19 | 5 | 5 | 0 | 0 | 10 | 0 | 0 | 0.01 |
| 20 | 5 | 5 | 0 | 0 | 0 | 10 | 0 | 0.01 |
| 21 | 5 | 5 | 0 | 0 | 5 | 5 | 0 | 0.01 |

To prepare the mixtures, the glucagon was dissolved in the respective buffers (phosphate, citrate, and glycine buffers, 5 mM, pH 3.0) at 10 mg/mL. The solution was then mixed in a 1:1 (v/v) ratio with various solutes, which were prepared at twice the desired concentration using corresponding buffer, in order to obtain a final glucagon concentration of 5 mg/mL and the final desired solute concentration. The solutions were then filtered through 0.2 μm Millipore PES membrane to remove insoluble materials. The sample preparations were conducted in a 4° C. cold room. The glucagon concentration and the purity were determined by RP- and Size-Exclusion (SE)-HPLC.

Example 2: Preparation of Dry Glucagon Powder by Freeze-Drying

The above formulations of Table 1 were pipetted (0.3 mL) into 3-ml lyophilization vials (13-mm ID). The formulations were lyophilized in a FTS Durastop freeze-drier (Stoneridge, N.Y.). Samples were frozen to about −40° C. at a ramp of 2.5° C./min and maintained for 2 hours (h) to allow sufficient freezing. The sample temperature was then increased to about −5° C. at a ramp of 2° C./min and held for 2 h as an annealing step. The temperature was then decreased to about −30° C. at a ramp of 1.5° C./min and the vacuum was turned on at 60 mTorr. The primary drying was set for 24 h. The temperature was gradually increased to about 40° C. at a ramp of 0.5° C./min and held for additional 10 h. After drying was complete, the vials were capped under vacuum using XX stoppers from the West Pharmaceutical company (product #10123524). None of the formulations showed any evidence of cake collapse following freeze-drying. These formulations were examined for physical and chemical stability immediately after freeze-drying, and again after two weeks of storage at about 60° C. to accelerate degradation.

Figure 1B:
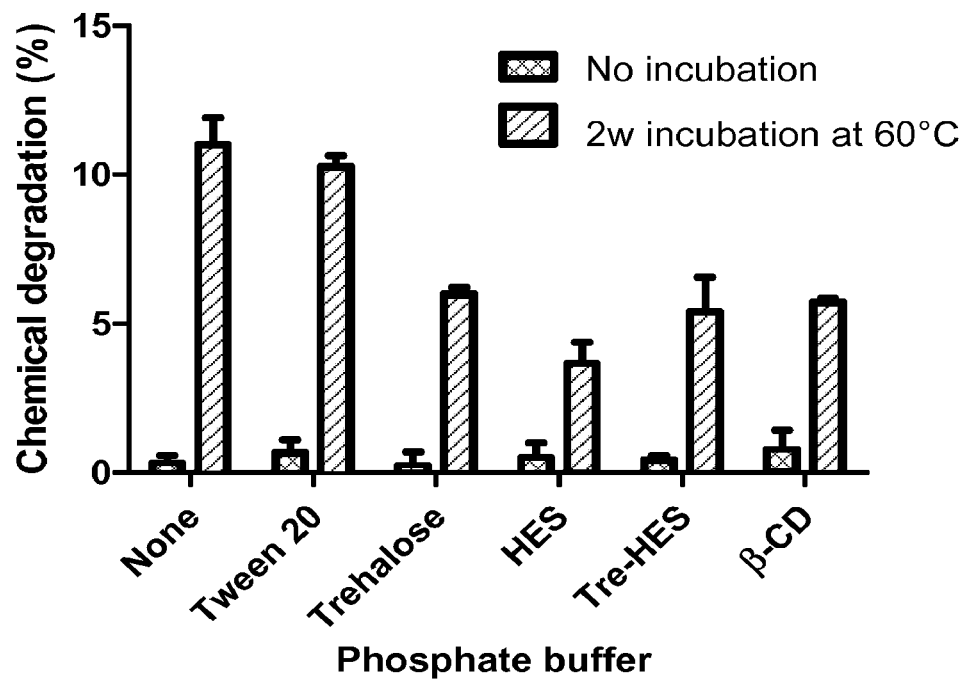
Figure 1C:
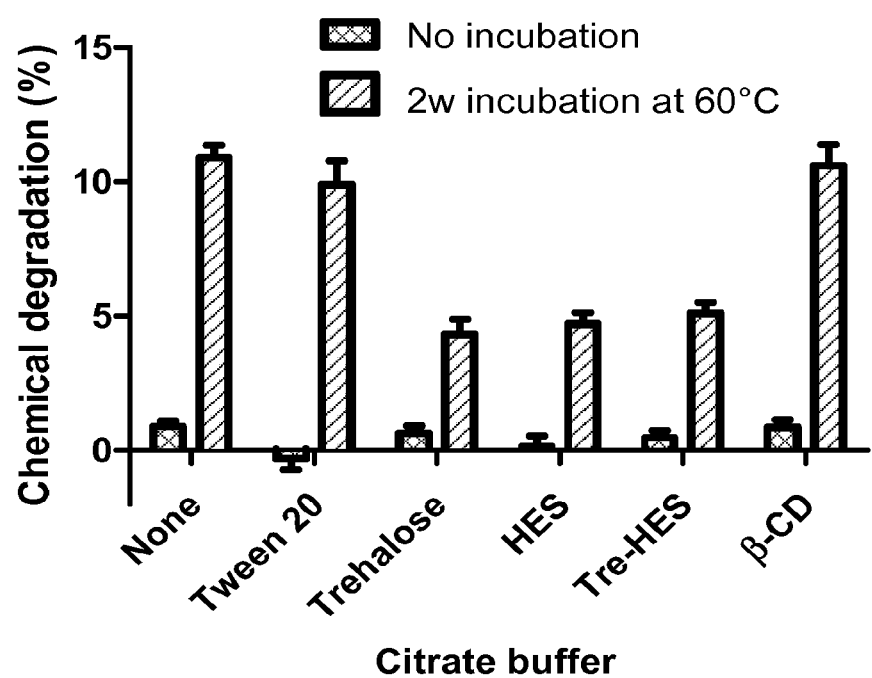

The chemical degradation of glucagon in different formulations was determined by RP-HPLC (see, FIG. 1). There was very little chemical degradation (<1%) during freeze-drying in all formulations. However, after incubation at 60° C. for 2 weeks, glucagon formulations without excipients showed significant amounts (about 11%) of chemical degradation in all three buffers (see, FIG. 1). These degradation products were mostly due to acid-catalyzed hydrolysis on Asp-X bonds as indicated by HPLC chromatograms. Oxidation products accounted for about 1% of chemical degradation after incubation. There was no significant difference among different buffers. Addition of 0.01% Tween only slightly decreased chemical degradation (about 10%) in all three buffers. Addition of carbohydrates, on the other hand, significantly decreased chemical degradation in most cases (3-6% chemical degradation after incubation at 60° C. for 2 weeks). For each specific buffer, different carbohydrates or the mixture of trehalose and HES showed similar effects of protection, except in citrate buffer, where formulations with β-CD showed no protection at all (11% chemical degradation). Formulations with carbohydrates in glycine buffer generally had lower chemical degradation (<4%) than the other two buffers evaluated, demonstrating a protective effect of the glycine buffer relative to the other two buffers when carbohydrates were added in the formulations.

Figure 2A:
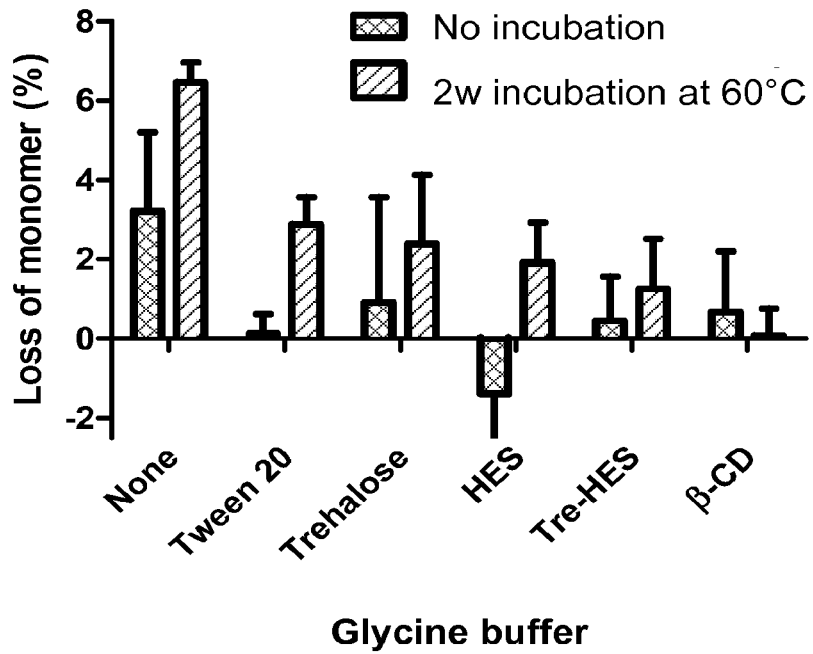
FIG. 2 illustrates the loss of monomeric glucagon following freeze-drying and incubation at 60° C. for 2 weeks as determined by SE-HPLC. The loss was determined as percent of monomeric glucagon relative to that present in solution prior to freeze-drying. (A) Glycine buffer; (B) Phosphate buffer; and (C) Citrate buffer. The values are the mean±SD from three independent experiments.
Figure 2B:
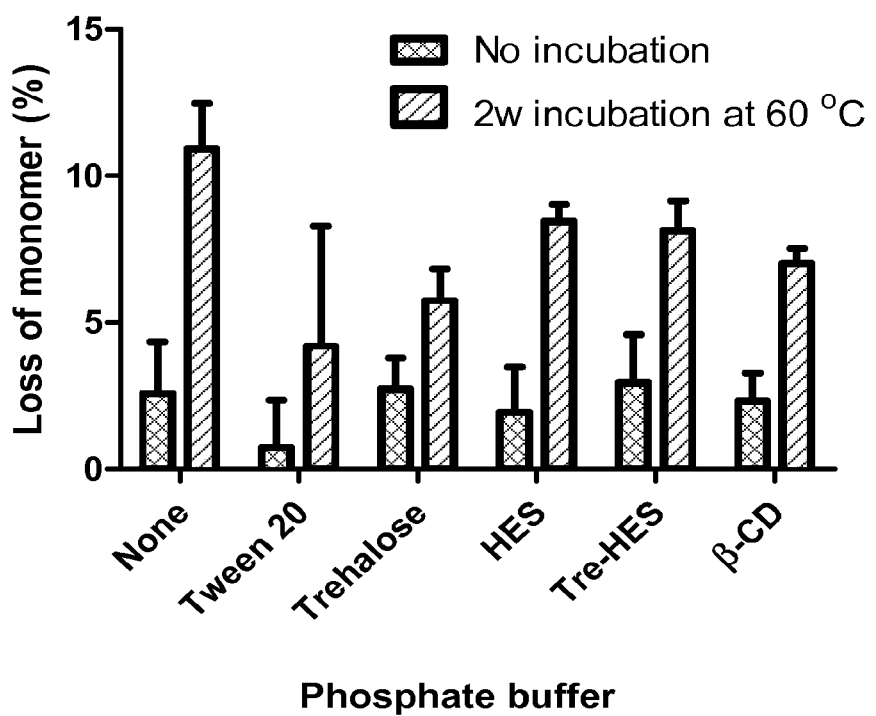
Figure 2C:
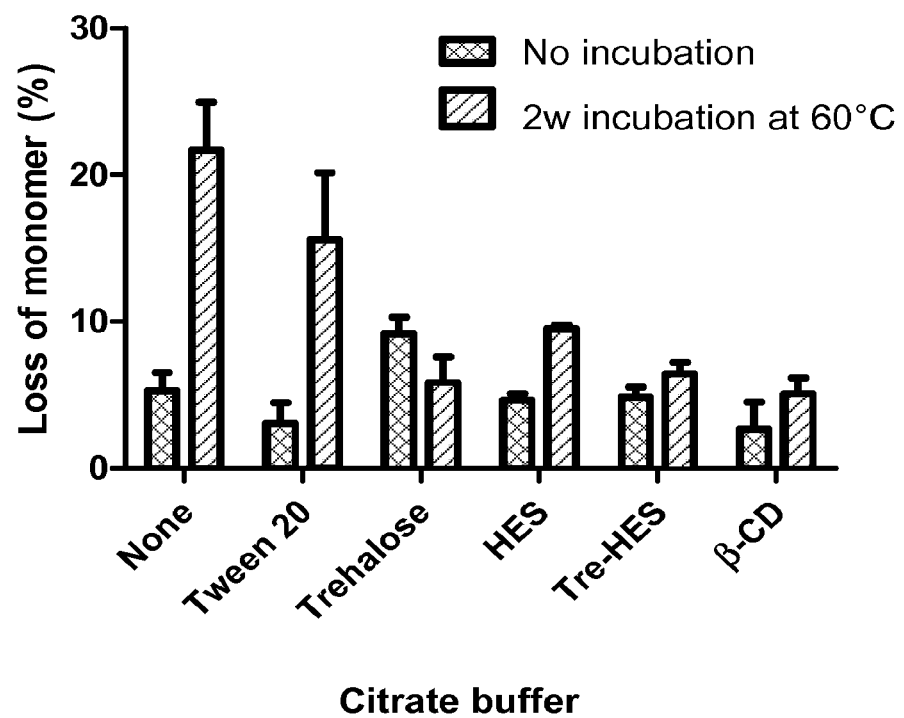

Size Exclusion-HPLC was used to quantitate the soluble and insoluble aggregates of glucagon formulations (see, FIG. 2). Surprisingly, there was almost no soluble aggregates in all cases (<0.5%). Therefore, the loss of monomer was mainly due to insoluble aggregates. Unlike chemical degradation, buffers had very significant effects on physical degradation during freeze-drying and after incubation at 60° C. for 2 weeks, especially when no excipient was added. During freeze-drying, there were about 3% insoluble aggregates in glycine and phosphate buffers, and more loss of monomer was observed (5%) in citrate buffer. Interestingly, buffer species had very significant effects on physical degradation of glucagon during freeze-drying and after incubation at 60° C. for 2 weeks, especially when no excipient was added. After incubation, formulation with glycine buffer exhibited lowest amount of aggregation (7%), followed by phosphate buffer (11%), and then by citrate buffer (22%). It is interesting that buffer alone had such an important influence on glucagon aggregation, especially considering the low concentration used in formulations (5 mM). Addition of 0.01% Tween 20 significantly inhibited aggregation in all three buffers (3%, 4%, and 16% loss of monomer for glycine, phosphate, and citrate buffers, respectively) following incubation.

Based on these results, several additional formulations were designed where the synergistic effects of glycine buffer, Tween 20 and carbohydrates could be evaluated. β-CD was not included since formulations with this carbohydrate all showed high turbidity. For a protein/peptide drug, turbidity is always a concern for both regulatory agency and patients as insoluble particles are not pharmaceutically elegant or may cause immunogenicity. Therefore three additional glucagon formulations having Tween 20 and trehalose, HES, or a mixture of trehalose and HES were selected.

As the glass transition temperature, Tg, of these three formulations were all very high (Table 5), and the values were similar to those without Tween 20 (Table 3). Addition of 0.01% Tween 20 did not have significant effects on Tg of these formulations, probably due to the very low amount added.

TABLE 5

Tg (° C.) of optimized glucagon formulations. The Tg values were determined as the midpoint where the change in specific heat occurred during the second heating process. The values are the mean ± SD from two independent experiments.

| Excipient | Glycine |
| --- | --- |
| Trehalose-Tween 20 | 105.7 ± 0.5 |
| HES-Tween 20 | 192.6 ± 0.1 |
| Tre-HES-Tween 20 | 121.8 ± 0.5 |

All these formulations showed no turbidity after reconstitution to 1 mg/mL in glycine buffer.

Figure 3A:
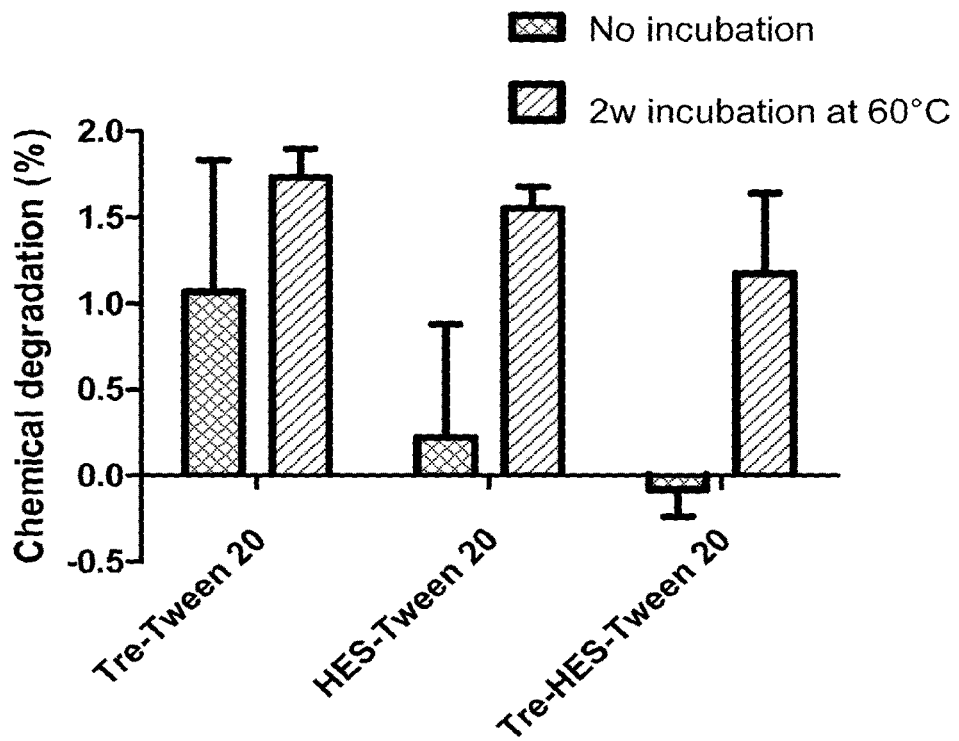
FIG. 3 illustrates the chemical and physical degradation of optimized glucagon formulations following freeze-drying and incubation. (A) chemical degradation as determined by RP-HPLC; and (B) physical degradation as determined by SE-HPLC.
Figure 3B:
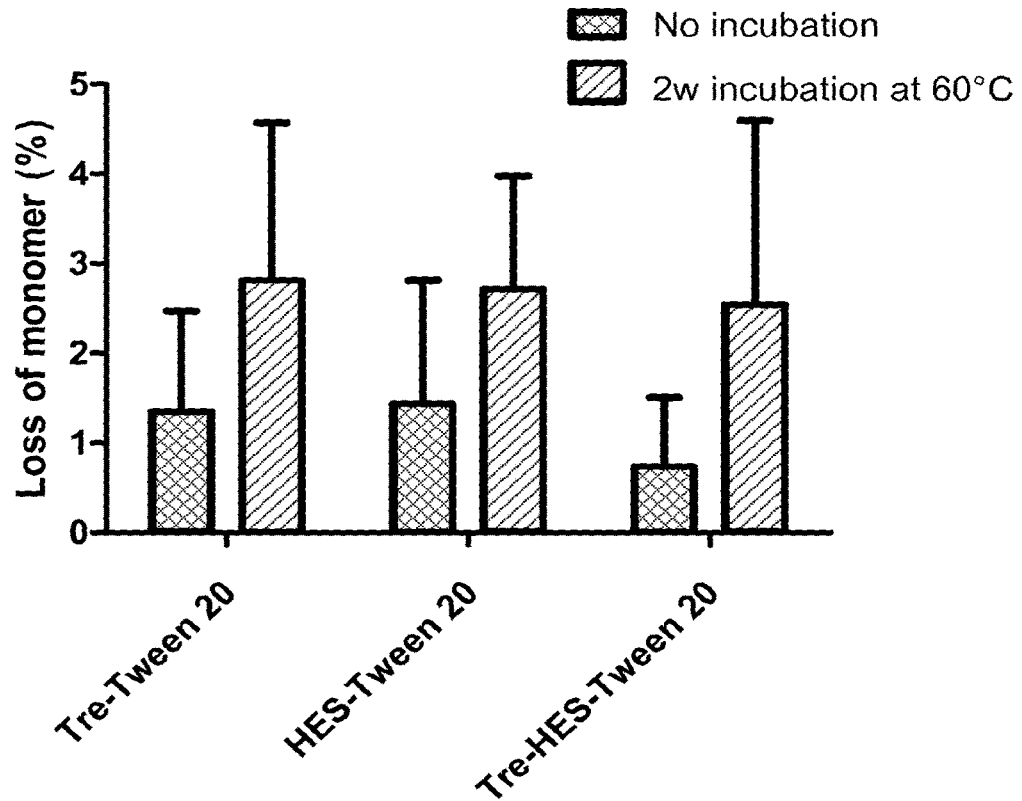

The combining effects of Tween 20 and carbohydrate were very significant in tennis terms of chemical stability of glucagon, as determined by RP-HPLC (see, FIG. 3). Less than 2% of degradation was observed for all three formulations. These formulations also exhibited a very low amount of aggregation, as determined by SE-HPLC (see, FIG. 3). Less than 3% of monomer loss was observed after incubation at 60° C. for 2 weeks.

Example 3: Preparation of Glucagon Formulations in Organic Diluents

Six of the dry powders made from solutions in Table 1 are chosen:
3. Buffer (glycine)+trehalose (200% relative to glucagon)
4. Buffer (glycine)+200% HES (relative to glucagon)
5. Buffer (glycine)+100% trehalose+100% HES (relative to glucagon)
19. Buffer (glycine)+Tween 20 (0.01% w/v)+trehalose (200% relative to glucagon)
20. Buffer (glycine)+Tween 20 (0.01% w/v)+200% HES (relative to glucagon)
21. Buffer (glycine)+Tween 20 (0.01% w/v)+100% trehalose+100% HES (relative to glucagon)

The dry powders are ground using a small mortar and pestle and sieved with a 90 micron sieve. The sieved samples are then placed in vials and mixed with diluents (triacetin or benzyl benzoate) to make a final solid concentration of 25 weight percent, i.e., in 2 mg dry powder, 6 mg of diluent is added). The procedures are conducted at room temperature in a dry box to keep the powder dry.

The vials were capped and incubated at room temperature (22-23° C.) and held for 2 weeks.

Figure 4:
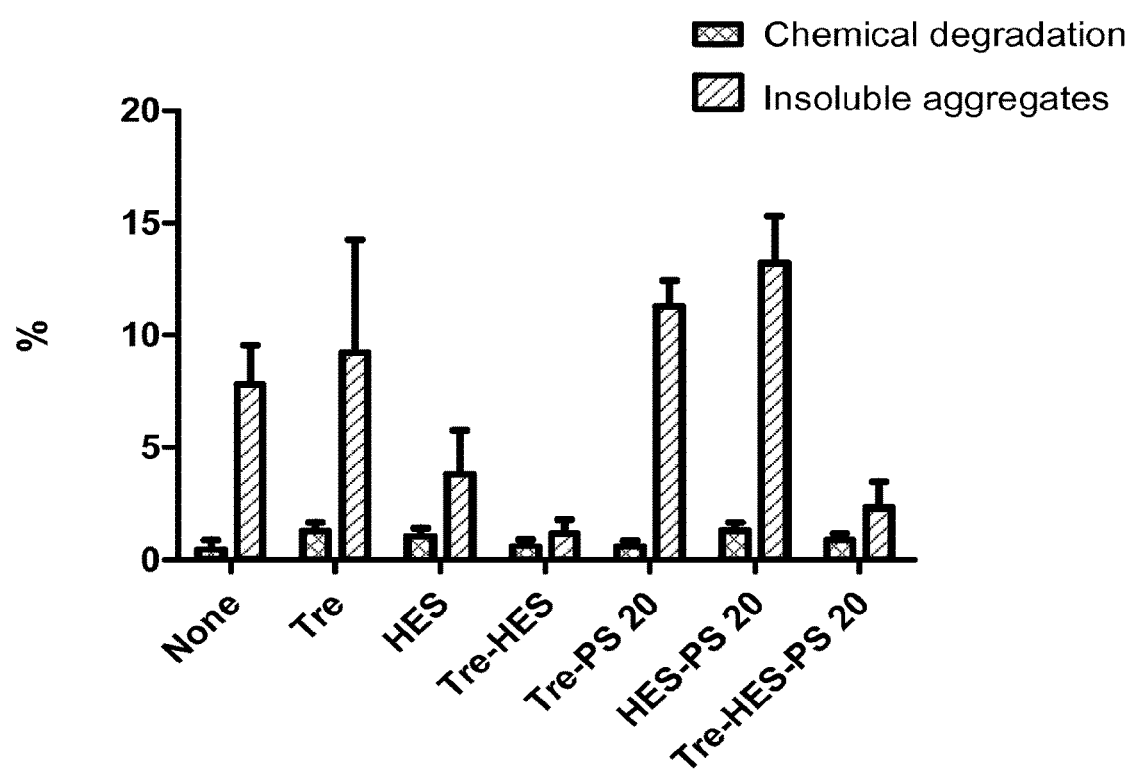
FIG. 4 illustrates the effects of carbohydrates and Polysorbate 20 on the chemical and physical stability of glucagon in triacetin, following incubation at room temperature as determined by RP-HPLC. The values are the mean±SEM from three independent experiments.
Figure 5:
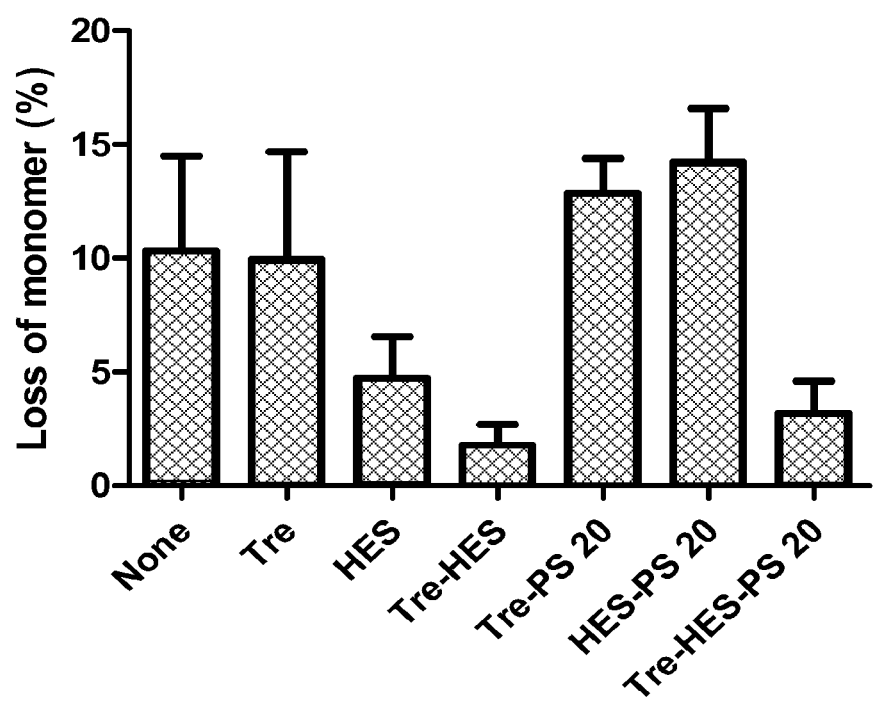
FIG. 5 illustrates the effects of carbohydrates and Polysorbate 20 on physical stability of glucagon in triacetin, following incubation at room temperature as determined by SE-HPLC. Soluble aggregate formation was minimal (<1%) for these formulations. The values are the mean±SEM from three independent experiments.

These dried glucagon powders are very stable when suspended in triacetin in terms of both chemical and physical stability (see, FIG. 4). All these formulations had minimal chemical degradation (less than 2%) for glucagon after incubation for 2 weeks. Without excipient, there was about 10% aggregation. The effect of carbohydrates on glucagon physical stability is shown in FIGS. 4 and 5. The mixture of trehalose and HES significantly inhibited aggregation compared with those without excipient. HES alone could also protect glucagon from aggregation, even though it was not as good as the mixture of trehalose and HES. Trehalose alone, on the other hand, could not protect glucagon from aggregation. Addition of Polysorbate 20 had a negative effect on the physical stability of glucagon as well. More aggregation was observed for formulations containing Polysorbate 20 than those without. Interestingly, a minimal amount of soluble aggregates was observed in all of the formulations, suggesting that triacetin inhibited the formulation of soluble aggregates.

Figure 6:
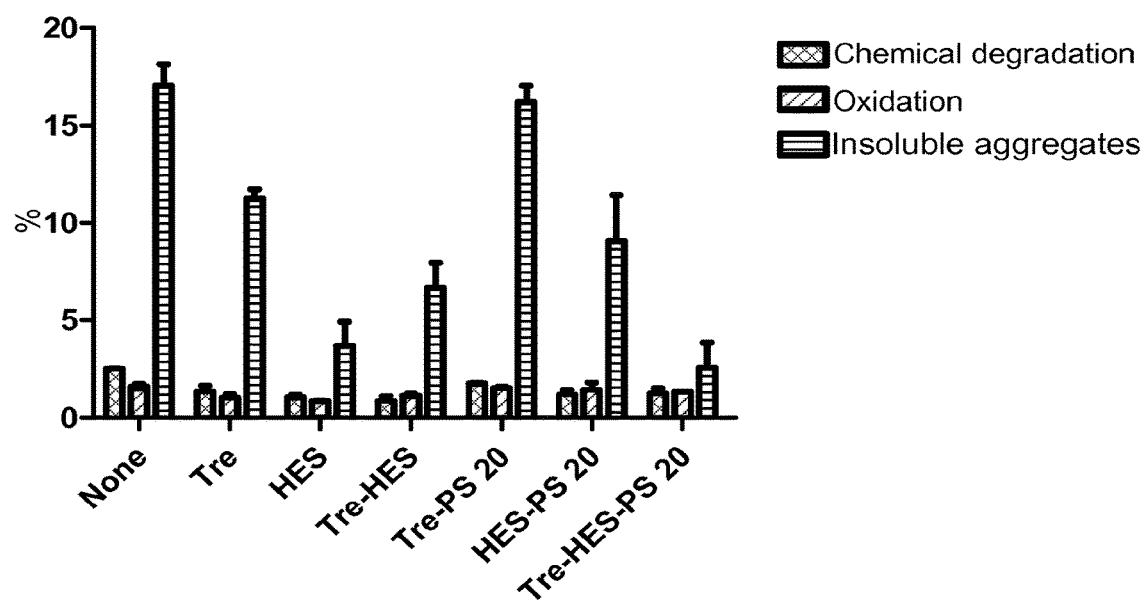
FIG. 6 illustrates the effects of carbohydrates and Polysorbate 20 on the chemical and physical stability of glucagon in benzyl benzoate, following incubation at room temperature as determined by RP-HPLC. The values are the mean±SEM from three independent experiments.
Figure 7:
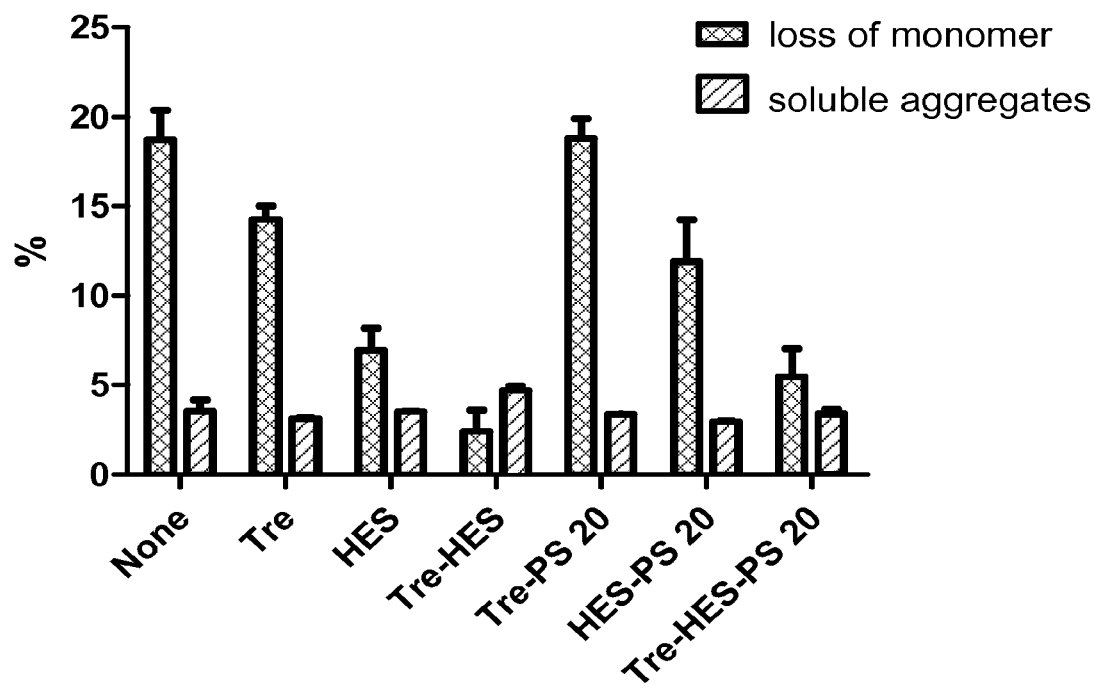
FIG. 7 illustrates the effects of carbohydrates and Polysorbate 20 on physical stability (soluble and insoluble aggregates) of glucagon in benzyl benzoate following incubation at room temperature as determined by SE-HPLC. The values are the mean±SEM from three independent experiments.

Glucagon had a similar stability profile when suspended in benzyl benzoate when compared with triacetin. The chemical degradation of glucagon was less than 3% in all cases. Without addition of carbohydrates, a significant amount of soluble glucagon (~15%) was lost, with addition of 5% soluble aggregate formation. Addition of carbohydrates generally could protect glucagon from aggregation. The mixture of trehalose and HES was the best formulation with almost no loss of soluble glucagon as determined by both RP- and SEC-HPLC. HES or trehalose alone could also protect glucagon from aggregation, but to a lesser extent compared with the mixture of HES and trehalose (see, FIGS. 6 and 7).

The final concentration of dissolved solid may range, for example, from 0.1% up to 70% (w/w), depending on the material and solvent used.

The invention has been described by way of illustration, and not by limitation. It is to be understood that the particular embodiments depicted in the figures and the terminology which has been used has been intended in a nature of words of description rather then of limitation. It is to be further understood that any combination of the ingredients/therapeutic agents described in the foregoing paragraphs are deemed to be encompassed by the appended claims. It is to be further understood that all specific embodiments of the injection device are deemed to be encompassed by the appended claims. Many modifications and variations of the present invention are possible in light of the above teachings. It is therefore to be understood that the obvious modifications are deemed to be encompass within the appended claims.

The invention claimed is:

1. A freeze-dried glucagon composition comprising:
   about 1,000 parts by mass glucagon, or a pharmaceutically acceptable salt thereof;
   about 1,000 parts by mass trehalose;
   about 1,000 parts by mass hydroxyethyl starch (HES); and
   about 75 parts by mass glycine buffer.

2. The freeze-dried glucagon composition of claim 1, further comprising an effective amount of an antioxidant selected from the group consisting of ascorbic acid, cysteine, methionine, monothioglycerol, sodium thiosulphate, sulfites, butylated hydroxytoluene (BHT), butylated hydroxyanisole (BHA), ascorbyl palmitate, propyl gallate, and vitamin E.

3. The freeze-dried glucagon composition of claim 1, further comprising an effective amount of a chelator selected from the group consisting of ethylenediaminetetraacetic acid (EDTA), tartaric acid and salts thereof, glycerin, and citric acid and salts thereof.

4. The freeze-dried glucagon composition of claim 1, further comprising an effective amount of a preservative selected from the group consisting of benzyl alcohols, methyl parabens and propyl parabens.

5. The freeze-dried glucagon composition of claim 1, wherein the glycine buffer establishes a pH of the freeze-dried glucagon composition of between about 2.0 and about 3.5.

6. The freeze-dried glucagon composition of claim 5, wherein the glycine buffer establishes a pH of the freeze-dried glucagon composition of about 3.0.

7. The freeze-dried glucagon composition of claim 1, further comprising about 2 parts by mass polysorbate 20.

8. A stable pharmaceutical formulation for parenteral injection consisting essentially of:
   about 1,000 parts by mass glucagon or a pharmaceutically acceptable salt thereof that has been freeze-dried with about 1,000 parts by mass trehalose, about 1,000 parts by mass hydroxyethyl starch, and about 75 parts by mass glycine buffer; and
   about 9,225 parts by mass pharmaceutically acceptable carrier or diluent comprising triacetin.

9. The stable pharmaceutical formulation of claim 8, wherein the glycine buffer has a pH of between about 2.0 and about 3.5.

10. The stable pharmaceutical formulation of claim 9, wherein the glycine buffer has a pH of about 3.0.

11. A stable pharmaceutical formulation for parenteral injection consisting essentially of:
   about 1,000 parts by mass glucagon or a pharmaceutically acceptable salt thereof that has been freeze-dried with about 1,000 parts by mass trehalose, about 1,000 parts by mass hydroxyethyl starch, about 75 parts by mass glycine buffer, and about 2 parts by mass polysorbate 20; and
   about 9,231 parts by mass pharmaceutically acceptable carrier or diluent comprising triacetin.

12. The stable pharmaceutical formulation of claim 11, wherein the glycine buffer has a pH of between about 2.0 and about 3.5.

13. The stable pharmaceutical formulation of claim 12, wherein the glycine buffer has a pH of about 3.0.

* * * * *